United States Patent [19]

Berntson

[11] Patent Number: 4,676,248

[45] Date of Patent: Jun. 30, 1987

[54] CIRCUIT FOR CONTROLLING A RECEIVER IN AN IMPLANTED DEVICE

[75] Inventor: Peter K. Berntson, Spring Lake Park, Minn.

[73] Assignee: Medtronic, Inc., Minneapolis, Minn.

[21] Appl. No.: 776,082

[22] Filed: Sep. 13, 1985

Related U.S. Application Data

[63] Continuation of Ser. No. 373,798, Apr. 30, 1982, abandoned.

[51] Int. Cl.⁴ .............................................. A61N 1/36
[52] U.S. Cl. .............................. 128/419 PG; 340/518
[58] Field of Search ............. 128/419 PG, 419 P, 903, 128/904, 423 R; 340/518, 825.1

[56] References Cited

U.S. PATENT DOCUMENTS

| | | | |
|---|---|---|---|
| 3,974,478 | 8/1976 | Griffith et al. | 340/825.1 |
| 4,040,013 | 8/1977 | Carlson | 340/825.1 |
| 4,109,246 | 8/1978 | Budrys et al. | 340/518 |
| 4,146,884 | 3/1979 | Kurn | 340/518 |
| 4,404,972 | 9/1983 | Gordon et al. | 128/419 PG |
| 4,539,992 | 9/1985 | Calfee et al. | 129/419 PG |

Primary Examiner—Edward M. Coven
Attorney, Agent, or Firm—Merchant, Gould, Smith, Edell, Welter & Schmidt

[57] ABSTRACT

A circuit for controlling a receiver in an implanted device and circuitry for decoding and storing received program signals is disclosed. In the circuit a control circuit periodically activates a receiver to surveil for remotely generating programming signals. When a program signal is detected by the receiver the control circuit latches the receiver into a continuously activated state for a predetermined time interval. If a reset code is detected from subsequently received signals the receiver is held in an activated condition for a further predetermined time interval. Decoding circuits including a timer are reset upon receipt of the refresh code and provide control over sequences of received programming data for use in programming the stimulation mode of output circuits in the implanted device.

12 Claims, 16 Drawing Figures

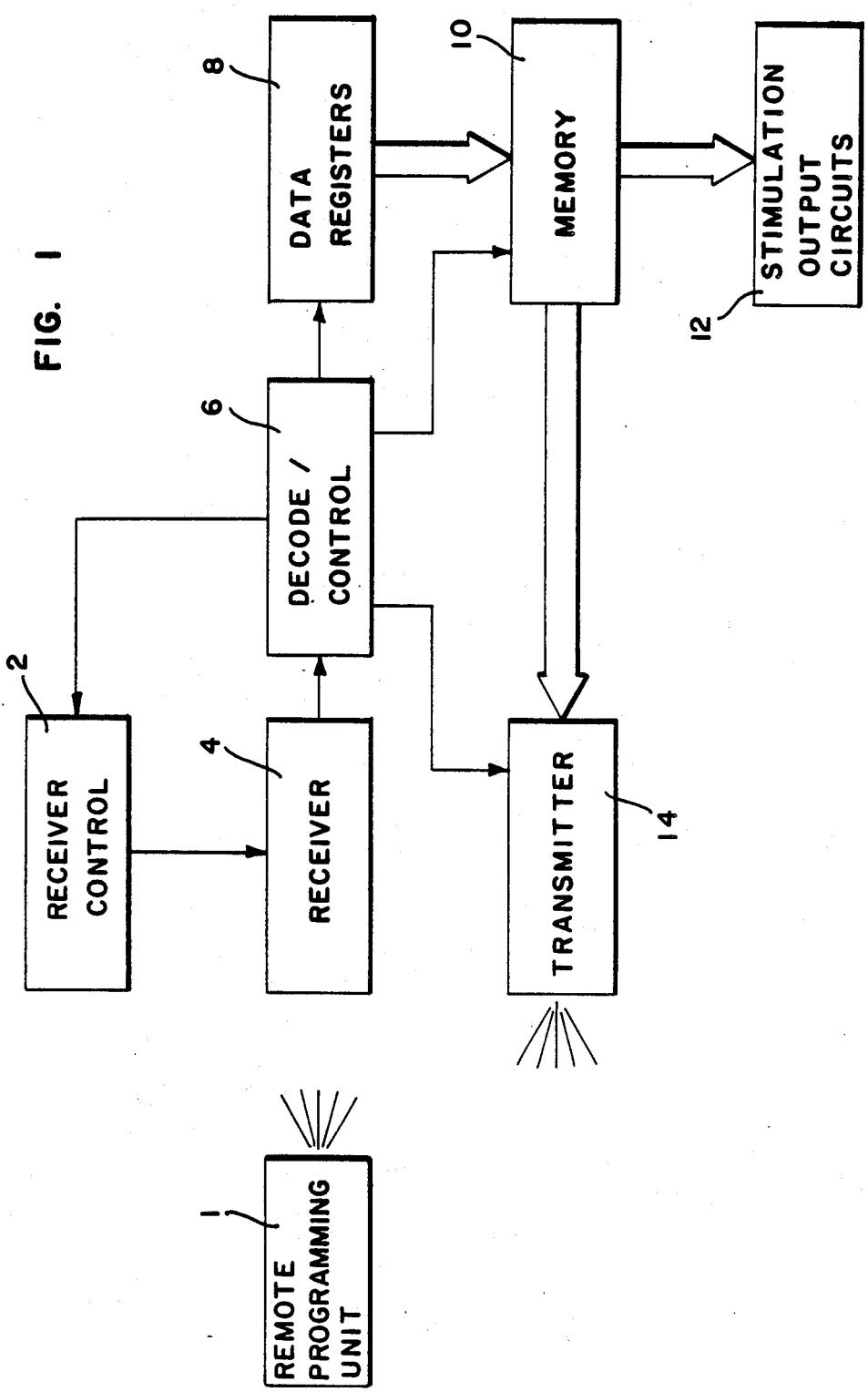

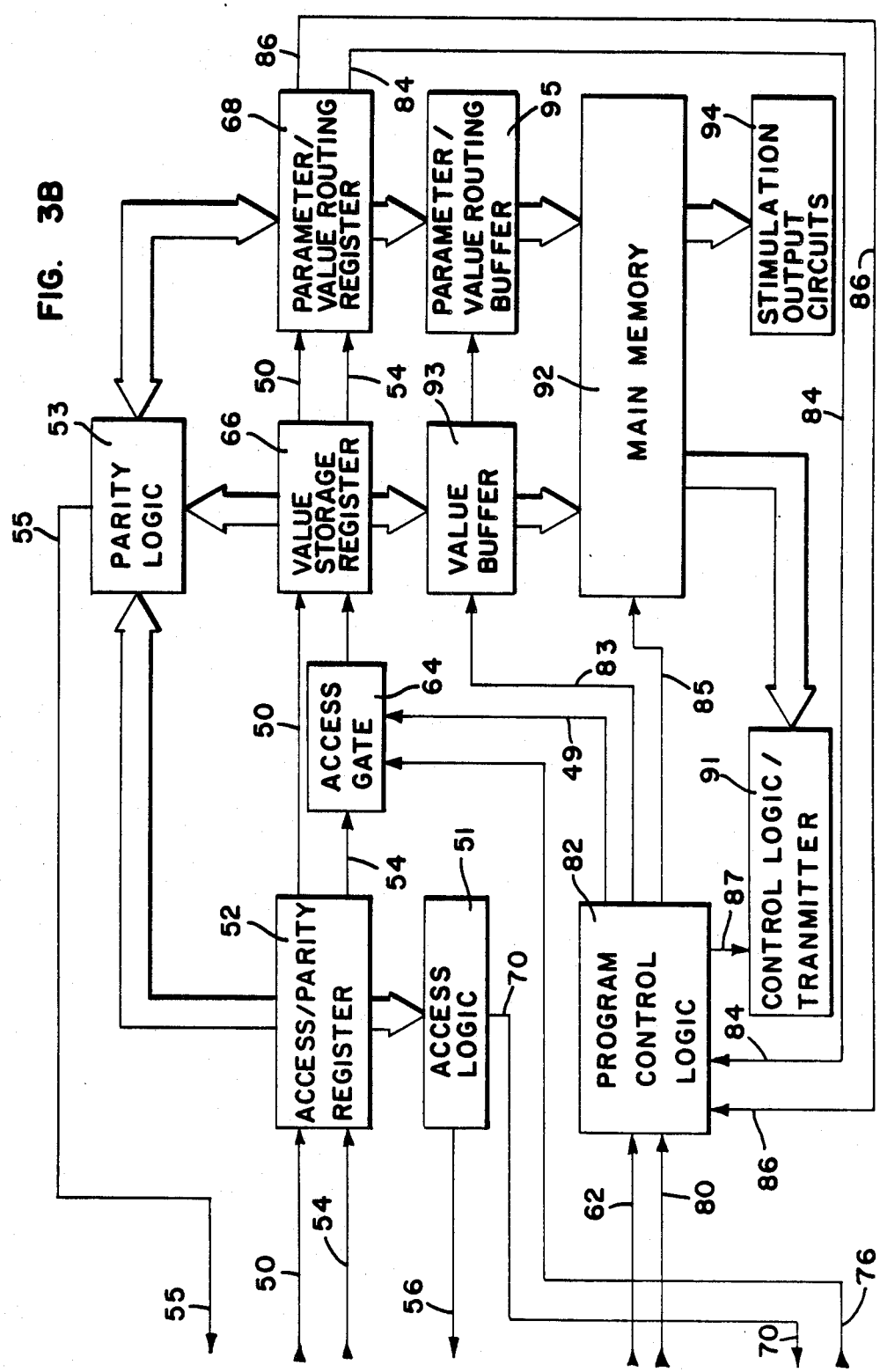

CIRCUIT FOR CONTROLLING A RECEIVER IN AN IMPLANTED DEVICE

This is a continuation, of application Ser. No. 373,798, filed Apr. 30, 1982, now abandoned.

TECHNICAL FIELD OF THE INVENTION

The present invention pertains to the field of implanted medical devices, and more particularly to controls for radio frequency receivers used in conjunction with implanted devices for receiving remotely generated programming signals.

BACKGROUND OF THE INVENTION

Spurred by the continuing microminiaturization of electronic circuits, remotely programmable implanted medical devices have gained wide popularity and acceptance among the medical profession. Remotely programmable pacemakers are one such type of implanted device made popular by their capacity to be adjusted after implantation without risky surgery. Remotely programmable implanted subcutaneous tissue stimulators are also popular because they allow for relatively frequent adjustments of stimulation modes and parameters to accomodate habituation and the like, without surgical procedures.

Generally, remotely programmable implanted units include a receiver for detecting and demodulating remotely generated radio frequency programming signals and decoding circuits for decoding the signals into digital impulses for control of the stimulation generating circuits. As required by the nature of radio frequency reception, receivers are analog circuits generally requiring greater power for proper operation than their digital counterparts. Also, the typical receiver is extremely sensitive to spurious or undesirable radio frequency signals emanating from various sources other than a remote programming device. If not accounted for these spurious signals can be mistaken for valid programming signals by the implanted device causing undesirable and possibly dangerous operation by the implanted unit.

To overcome these problems, implanted units typically include a magnetically activated reed switch for selectively energizing the receiver during a remote programming operation. Thus, the receiver remains deenergized, so as to conserve the limited power resources of the implanted device, and non-responsive to possibly dangerous spurious radio frequency signals, between remote programming operations.

While the use of magnetically operable mechanical reed switches is effective in overcoming the above noted problems, there are several drawbacks associated therewith. For example, reed switches are mechanical devices which in general are less reliable or more failure prone than electronic circuits. Thus, the reed switch is typically the "weakest link" in a remotely programmable implanted device. Also, attempts to reduce the size and weight of implanted devices have been inhibited by the need for reed switches, which have proven extremely difficult to miniaturize. Furthermore, utilizing a reed switch to energize the receiver section requires that the remote programming head contain a substantial magnet, adding to its weight and therefore making more difficult its positioning during a programming operation.

In response to the above described disadvantages of reed switches, the present invention provides a receiver circuit not requiring a reed switch for activation thereof, which is low in power consumption and which effectively eliminates erronous programming of the implanted device by spurious radio frequency signals.

In addition to improving the reliability and space requirements of the receiver circuit, the present invention makes way for the use of reed switches in less critical functions, for example a simple on-off control for the implanted device. Because the same on-off control may be accomplished through regular programming, the reed switch provides an additional or back-up control for the physician, or means for allowing the patient, with a simple magnet, to exercise limited control over the implanted device. In the case where a malfunction of the implanted device is potentially life-threatening, it is contemplated that the suggested magnetically operated on-off reed switch will provide an additional degree of safety to the patient by permitting immediate deactivation of the device.

SUMMARY OF THE INVENTION

The present invention provides a circuit for controlling a receiver in an implanted device of the programmable type. The circuit includes means for causing the receiver of the implanted device to the intermittently activated to survey for remotely generated programming signals and for causing the receiver to be continuously activated for at least one predetermined time interval when a programming signal is detected by the receiver. According to one aspect of the invention, a reset circuit responsive to a remotely generated reset code comprising more than one programming signal provides means for causing the receiver to be continuously activated for a further predetermined time interval. Decoding circuits are connected to the receiver for translating remotely generated programming sequences into digital impulses for control of the stimulation output circuits of the implanted device. In the preferred embodiment, the decoding circuits include a counter for counting incoming programming signals and verification circuits synchronized in part by the counter for testing their accuracy. According to another aspect of the invention, programmed data may be either permanently recorded in the memory of the implanted unit or temporarily linked to the stimulation output control circuits. Linkage may be maintained by continually providing a reset code to a timer circuit provided for cancelling received programming data. The timer circuit is reset at the beginning of a programming sequence, and provides a means for automatically cancelling programming data which does not get transferred to permanent memory. Thus, it will be seen that the present invention provides a means for remotely activating the receiver of an implanted device equivalent in function and superior in reliability to a magnetic reed switch.

BRIEF DESCRIPTION OF THE DRAWING

In the drawing, FIG. 1 is a conceptual block diagram of the present invention;

DETAILED DESCRIPTION OF THE INVENTION

FIG. 1 is a conceptual block diagram of the preferred embodiment of the present invention. In the Figure, there is shown a receiver 4 for receiving RF pulses generated by a remote programming unit 1. Received pulses are demodulated and decoded in decode/control 6, into useable digital programming data. A receiver control circuit 2 is connected to receiver 4 for causing it to operate in one of two modes. In a first mode, receiver 4 is strobed, ie. periodically activated for a relatively short period of time, so as to provide a virtually, but not actually, continuous "watch" for incoming programming pulses from remote programming unit 1. In the preferred embodiment, the duty cycle of the receiver is less than one percent so that the power requirement of the receiver while operating in the watch mode is within the limitations dictated by state of the art power sources or batteries utilized in implanted devices. In a second mode, receiver 4 is latched into a static on-condition by a "wake-up" pulse from programming unit 1. Receiver 4 remains latched in the on-condition for a time interval controlled by decode/control 6 and RF program pulses received from the programming unit 1, and thereafter returns to the first "watch" mode. Thus, the present invention provides an essentially continuous surveillance, by periodically strobing the receiver, for incoming program pulses during the relatively long intervals between programming operations, and an active programming mode in which receiver 4 is latched in a static on-condition for reception of closely grouped programming pulses during programming operations.

Figure 4:
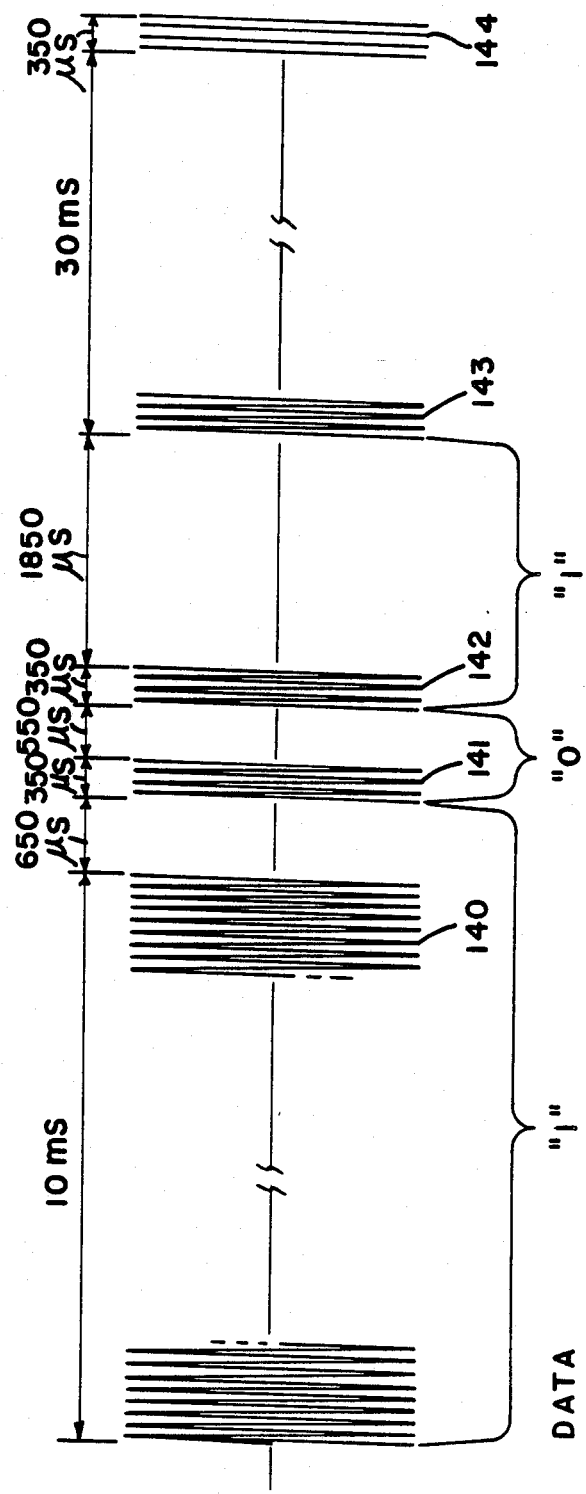
FIG. 4 is a graphical representation of RF programming signals utilized by the present invention.

Referring to FIG. 4, there is shown a wake-up pulse 140 and subsequent wake-up code pulses 141–143. In the preferred embodiment, pulse 140 has a duration of 10 milliseconds so as to assure coincidence with at least one of the receiver strobe pulses, which in the preferred embodiment occur at 4 millisecond intervals and have a duration of 30.5 microseconds. Coincidence of the wake-up pulse 140 and a strobe pulse causes receiver 4 to latch in the on-condition and to convey the remaining duration of the wake-up pulse to the decode/control circuit 6 for storage in the data registers 8.

While latched in the on-condition receiver 4 conveys received RF pulses to decode/control 6, which is connected to the first of the stages, 22 in the preferred embodiment, of data registers 8. Utilizing timing considerations respecting the duration between received input pulses, circuit 6 produces programming data consisting of logic highs and lows at its output, to be clocked into the register 8. Receiver 4 remains in the on-condition until a reset signal is received from control circuit 2, which is controlled by reset-timers and circuits in decode/control circuit 6.

The series of pulses 140–143 load the first three stages of register 8 with a digital wake-up code, binary 101 in the preferred embodiment. Providing that the pulse count is equal to 4 (programming bit count=3), a refresh or reset signal is conveyed to the decode/control circuit 6 and the receiver control 2, whereby the circuits are initialized for the receipt of programming data pulses, the first of which is represented by pulse 144, for control of the stimulation output circuits. The refresh signal also provides the reset for the timers of control 6 to provide an active receiving mode for at least one predetermined time interval, allowing for a sequence of RF programming pulses to be received and decoded. In the preferred embodiment, a delay of 30 ms from pulse 143 to pulse 144 is provided to allow sufficient time for the circuits to initialize properly.

In the preferred embodiment, programming code is generated by the programmer in 32 bit sequences, 14 bits of which are program data and 16 bits of which control access to the memory and to the control circuits of the stimulation output circuits; the first two bits of each sequence do not contain programming information and are disregarded by the programming decoding circuits. Each sequence is divided into two transmission blocks, of 24 bits and 8 bits, with the 8 bit block supplanting or replacing the last 8 bits of the first block, which normally reside in the first 8 stages of register 8 after a complete first block has been clocked in. The last 8 bits of the first block of data comprise an access code, which when correct, locks 14 of the first 16 bits i.e. the program data, into the last 14 stages of register 8, the first two bits being shifted out of the register. With the last 14 stages latched the first 8 stages of register 8 are rewritten with the second block of program pulses, which make up 8 bits of parity information. If parity is correct, the data present in the last 14 stages of register 8 is either permanently written into memory 10 or temporarily linked to the control circuits of output circuits 12. The particular operation performed is controlled by one of the first two bits of the latched programming data.

The 14 programming bits comprise 8 bits of "value" information and 6 bits of "routing" information. The routing information instructs the stimulationcontrol and memory circuits as to which programmable parameter, e.g. pulse rate or width, the value information is to be assigned.

In the preferred embodiment, a transmitter 14 provides for the transmission of programmed data from the implanted unit to the remote programming unit for verification of recently programmed data stored in memory. Typically, a verification transmission is executed at the end of a 32 bit programming sequence, but may be delayed by the programming data until a series of programming sequences, each comprising 32 bits, is completed.

Figure 2A:
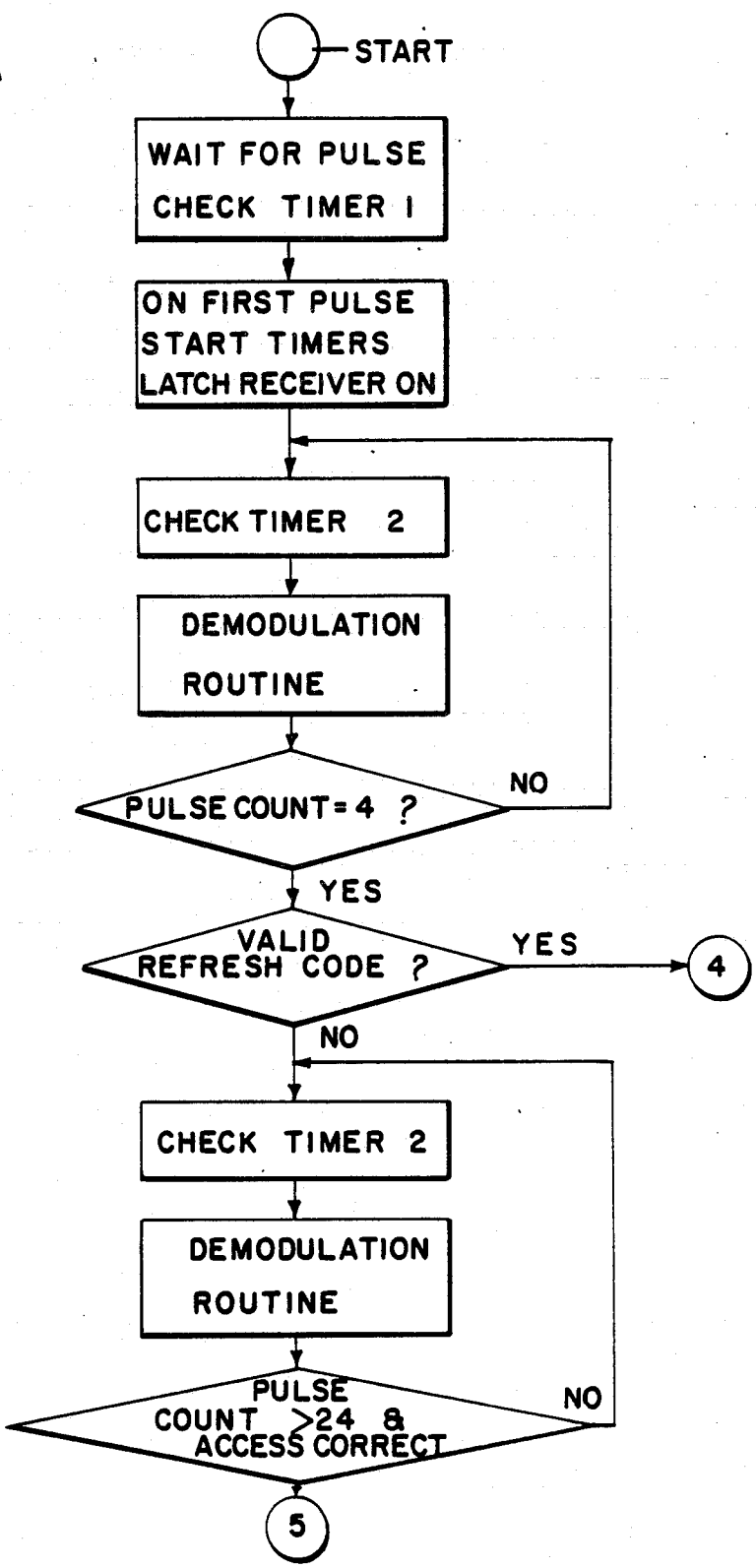
FIGS. 2A, 2B and 2C are a flow chart diagram of the circuit operation of the present invention.
Figure 2B:
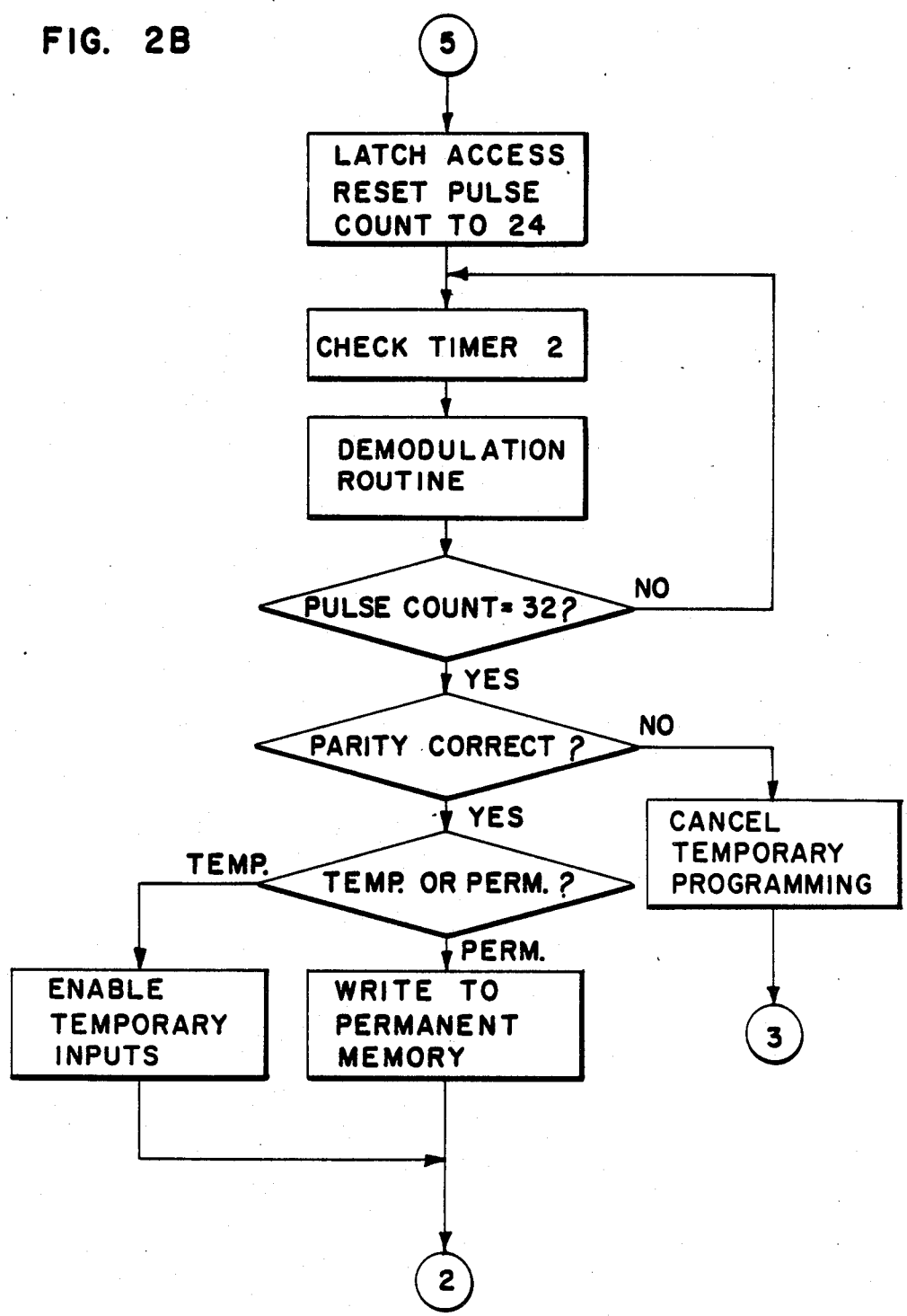
Figure 2C:
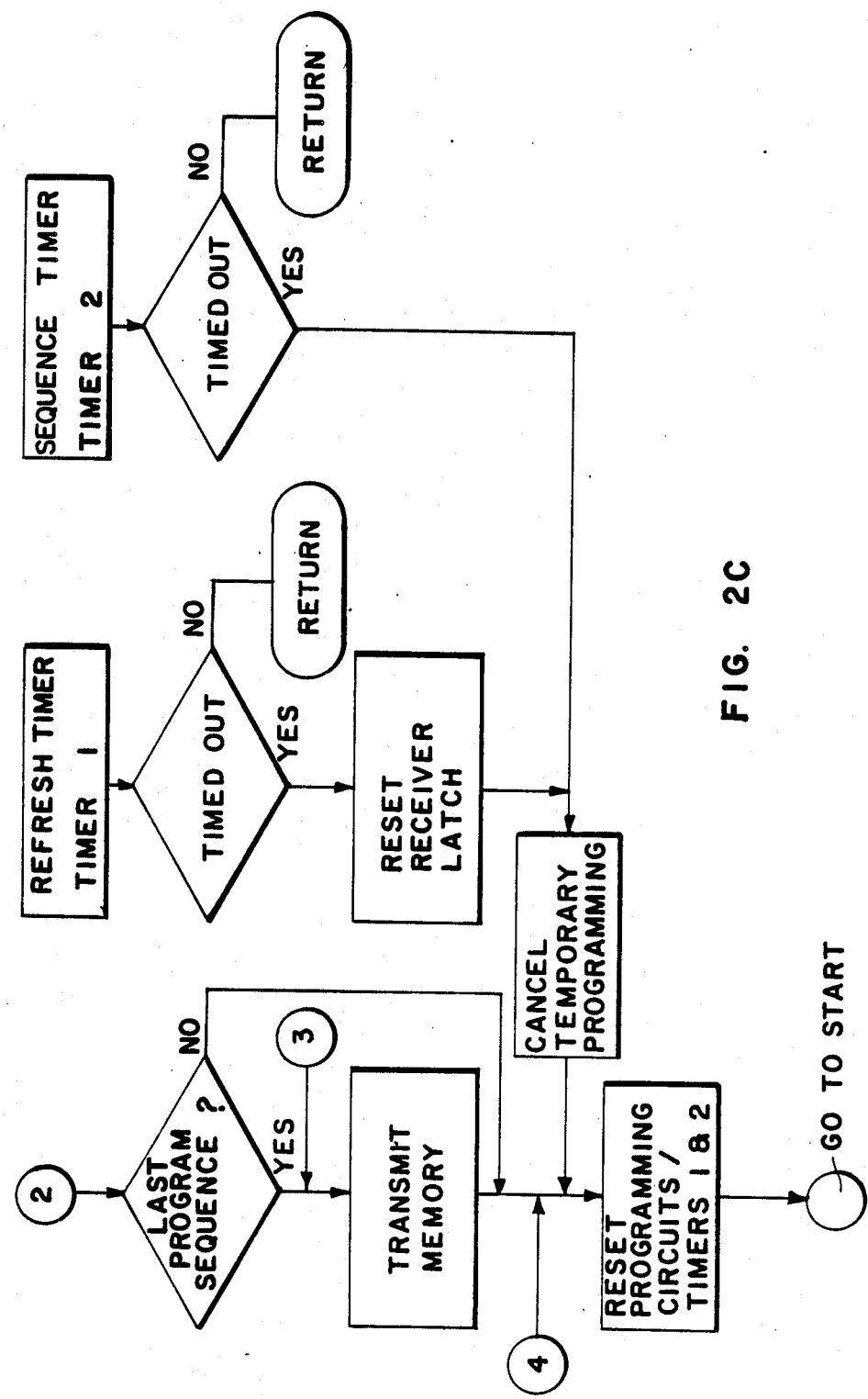

FIGS. 2A, 2B and 2C comprise a flow chart diagram corresponding to the operation of the electronic circuitry of the present invention. Each step or block in the flow chart corresponds to a particular function of the circuitry, and in general may be identified with a particular section or group of circuits in the detailed schematic diagram. To aid in the explanation of the operation of the present invention, the flow chart of FIGS. 2A, 2B and 2C will be explained in conjunction with FIGS. 3A and 3B, which comprise a detailed block diagram of the circuits of the present invention. However, it shall be understood that the flow chart and the block diagram are primarily intended as an aid in explaining the operation of the circuits, and a full or complete understanding is not possible without resort to the detailed schematic diagrams.

Throughout the flow chart, there are references to timers 1 and 2, which are represented in FIG. 2C. In general, these timers provide a check on the proper flow of programming data into the programming section, and means for resetting or reinitializing the various decoding circuits when an error is suspected or in fact has occurred, or at the end of a programming operation. Timer 1 and timer 2 correspond refresh timer 40 and to sequence timer 69 respectively, of FIG. 3A. Referring to the flow chart, it will be seen that upon timing out either timer will cause a cancellation of temporary programming and a reset of the programming circuits. A time out of timer 1 will additionally cause a reset of the receiver latch, putting the receiver back into its "watch" mode. Functionally speaking, timer 2, i.e., the sequence timer 69, has a time out period related to the time period required for a single 32 bit programming sequence to occur. If the sequence is not completed within the time provided, an error is assumed and the programming circuits reset. Timer 1, i.e. the refresh timer 40, has a longer time out period than timer 2, and has as its primary function the reset of the receiver latch signal whereby the receiver is put back into its "watch" mode at the end of a programming operation.

Figure 3A:
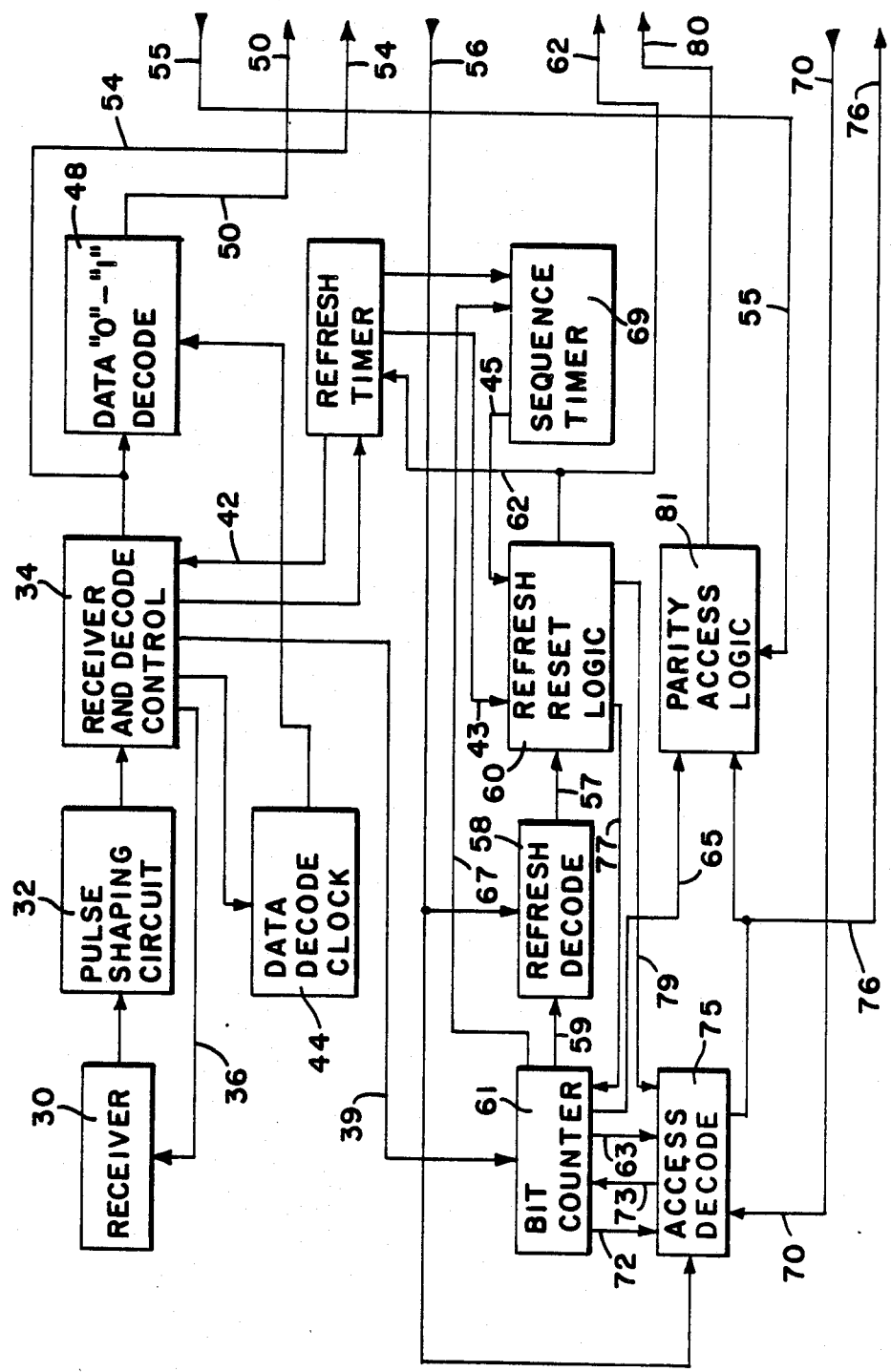
FIGS. 3A and 3B are a detailed block diagram of the electronic circuits of the present invention.

In FIG. 3A, timer 40 is shown having an output signal path 42 for input to the receiver and decode control 34 and an output signal path 43 for input to the referesh reset logic 60. Signal path 42 conveys the receiver-latch reset signal from timer 40 to the receiver and decode control circuit 34, which in turn causes the receiver 30 activation signal, carried on signal path 36, to be reset. Signal path 43 provides for the reset of refresh logic 60, to cancel any temporary programming which may be linked to the stimulation output circuits, and for the reset of bit counter 61 and access decode circuit 75, via signal paths 77 and 79 respectively from logic 60. Timer 69 has an analogous connection to refresh reset logic 60 through signal path 45, but does not connect to receiver decode control 34, as timer 40 does.

The first step or block in the flow chart is found in FIG. 2A immediately below the entry point labeled "START". This block, entitled "Wait for Pulse-Check Timer 1", corresponds to or represents those circuits of the present invention which monitor the influx of programming pulses from the remote programming unit 40 and those circuits which provide for the receiver strobe operation of the present invention.

As indicated by the second block in the flow chart, the first detected programming pulse starts timers 1 and 2 and latches the receiver on. In general, the receiver and decode control 34 of FIG. 3A corresponds in function to the first two above mentioned flow chart steps. In the receiver strobe mode, control 34 periodically activates or enables the receiver 30. When the strobe signal coincides with a programming pulse at receiver 30, the programming pulse is converted to a useable digital signal in pulse shaping circuit 32 and conveyed to control 34, which in turn latches receiver 30 "on" via signal path 36. This first pulse also starts timer 40 via signal path 37, and timer 69 via signal path 39, bit counter 61 and signal path 67.

With receiver 30 latched in an on-condition, subsequent programming pulses are conveyed through pulse shaping circuit 32 and receiver and decode control circuit 34 to the data "0"–"1" decode circuit 48, so that they may be decoded into usable programming data bits for input to the various program registers. The flow chart loop comprising the steps of "Check Timer 2", "Demodulation routine" and "Pulse Count=4?" corresponds to the circuits which receive, demodulate, count and clock programming pulses into the storage registers until a pulse count equal to 4 is detected. In the case where a pulse count equal to 4 is not reached before timer 2 times out, any temporary link of programming data to the control inputs of the stimulation output circuit is cancelled and the programming decode circuit are reset. Temporary or permanent programming of the stimulation output circuits is provided for by a program control circuit to be hereinlater described.

Figure 3B:
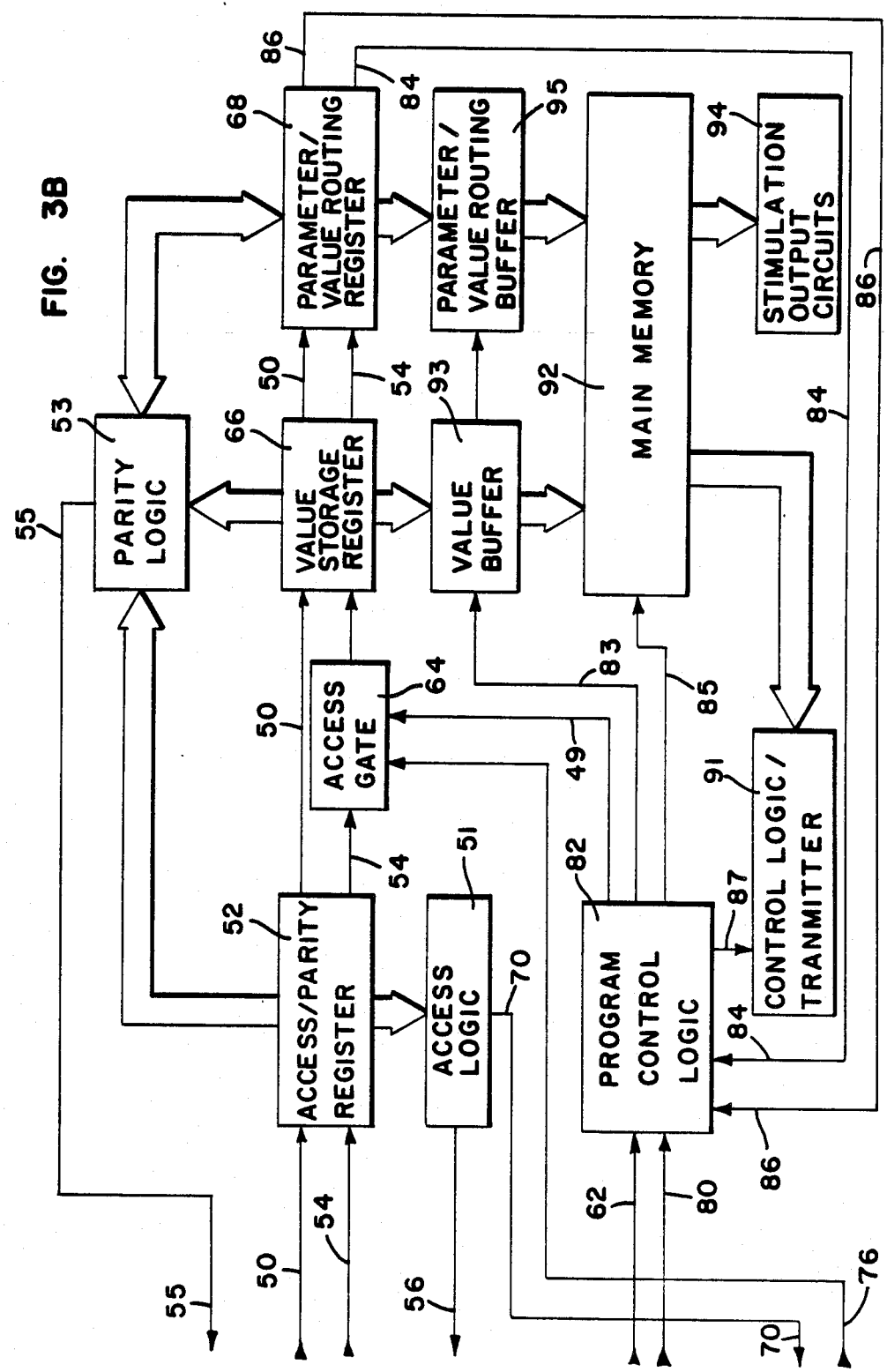

In FIGS. 3A and 3B those circuits of the block diagram corresponding to the above mentioned program registers, counter and control circuit are illustrated. Access/parity register 52, value storage register 66 and parameter/value routing register 68 provide a 22 bit shift register, with access gate 64 controlling the serial flow of data bits from circuit 52 to registers 66 and 68. Registers 66 and 68 receive the value and routing programming bits respectively. Circuit 52 receives serial data from decode circuit 48 through signal path 50. Bit counter 61 is incremented via signal path 39 from decode control 34, in response to each program pulse received. As previously described, timer 69 provides a reset signal to the reset logic 60, which in turn resets bit counter 61 and access decode circuits 75. Decode circuit 75 is connected to parity access logic 81 through signal path 76. Program control logic 82 is connected to the main memory 92, and to the refresh reset logic 60 and the parity access logic 81, through signal paths 62 and 80 respectively. Program control logic 82 controls the main memory via signal path 85 so that received programming data may either be permanently written into the main memory 92 or may be temporarily channeled or linked through memory 92 for control of the stimulation output circuits 94 for a limited amount of time, to enable the operator, usually the physician, to monitor the effect of the programming data on the output circuits, instead of or before writing the data permanently into memory 92.

In the case where the pulse count in bit counter 61 reaches 4 (bit count=3) before a time out of timer 2, circuit execution continues to the decision block "Valid Refresh Code?". If a valid refresh code has been received and properly clocked into the first 3 stages of register 52 an output indicative of such is generated by access logic 51 on signal path 56 for input to refresh decode 58, along with a pulse count=4 signal through path 59 from bit counter 61. These signals cause refresh decode 58 to generate a reset signal on signal path 57, for input to the refresh reset logic 60. In response thereto, logic 60 generates a reset signal on signal path 62 for resetting timer 40 and a reset signal to bit counter 61 through signal path 77. Resetting bit counter 61 (to a pulse count equal to 0) additionally causes the reset of timer 69 through signal path 67. Thus, the occurrence of a valid refresh code and a pulse count=4 signal causes the reset of timer 40, timer 69 and bit counter 61, as indicated in the decision block found directly beneath entry point 4 in FIG. 2C. As also indicated in the flow chart, circuit execution then reverts or begins again at the start point in anticipation of further programming data.

In the case where a valid refresh code does not occur simultaneously with a pulse count=4 circuit execution continues to the loop comprising "Check Timer 2", "Demodulation Routine", "Pulse Count≧24" and "Access Correct". Circuit execution may reach this loop under any one of two circumstances. In the first circumstance, a valid refresh code has been previously received and circuit execution has been restarted from the start entry point, so that the pulse count of 4 indicates the first three bits of a 32 bit programming sequence have been received. By definition, the first 3 bits of a valid programming sequence cannot be the binary 101 refresh code and therefore circuit execution continues through the "no" branch of the decision block "Valid Refresh Code?". In the second circumstance, the refresh code necessary to reset the timers and initialize for a programming sequence has not been previously received, so timer 69 (timer 2) times out before the receipt of the entire programming sequence, causing any temporary programming to be cancelled and causing the reset of the programming circuits. As indicated in FIG. 2C, circuit execution will then again proceed to the start point with the circuits in a reset or initialized mode.

Referring back to the first circumstance, that is the one in which value programming data is being received, demodulation and clocking of the data will continue under normal circumstances until a pulse count greater than or equal to 24 is detected by bit counter 61. As indicated in FIG. 3B, the data bits are clocked through the register 52, access gate 64 and into value storage register 66 and parameter value routing register 68. The clocking signal for registers 52, 66 and 68 is conveyed through signal path 54 from the output of receiver and decode control 34. A count greater than or equal to 24 causes bit counter 61 to initiate a check on the code residing in register 52, via signal path 72. Signal path 70 is connected to a logic array in register 51 which produces a access signal when a predetermined access code resides in the 8 stages of register 52. In the case where the pulse count is greater than or equal to 24 and the access signal is produced, access decode 75 produces an access-latched signal on signal path 76 for input to the access gate 64. Thereafter, no futher program data may be clocked into value storage register 66 or parameter/value routing register 68 until the access gate is reset or opened via signal path 49 from program control logic 82. Signal path 76 is also connected to parity access logic 81 for reasons which will be hereinlater described. A further signal is generated by access decode 75 for input to bit counter 61 through signal path 73. This signal causes bit counter 61 to be set at a pulse count of 24, as is required for proper continuation of circuit execution. It will be observed that although an access code will typically be received on the 24th bit following the end of the last wake-up pulse, in some circumstances spurious intervening bits may occur after the wake-up pulse but before the first pulse of the 32 bit programming sequence. These intervening bits are not a problem providing that the 16 bits arriving previous to the access code are accurate, as the intervening bits will be shifted out of the end stages of register 52.

As indicated in FIG. 2B at entry point 5, which continues from the exit point 5 of FIG. 2A, the previously described circuit operation is indicated in the first decision block labeled "Latch access - reset pulse count to 24". The next circuit execution loop comprises the blocks of "Check Timer 2", "Demodulation Routine", and "Pulse Count=32?". In this loop, the trailing 8 bits of parity information are received, demodulated and clocked into register 52. Under normal circumstances, timer 2 will not time out before the bits are clocked in, but in the event of a discontinuity or unexpected delay in the programming sequence, the reset and cancel operations previously described are executed. When a pulse count equal to 32 is detected by bit counter 61, an output signal is generated on signal path 65 for input to the parity access logic 81.

The decision block "Parity Correct?" corresponds to the function of the parity access logic 81. When both a pulse count equal to 32 signal and an access latch signal are present on signal paths 65 and 76 respectively, parity access logic 81 responds to the signal produced by parity logic 53 on signal path 55. Parity logic 53 is connected via data buses to register and logic 52, value storage register 66 and parameter/value routing register 68. In the case where the logic 53 determines that proper parity has been received, a parity signal on signal path 55 causes parity access logic 81 to generate a parity correct signal on signal path 80 for input to the program control logic 82. In the case where parity is not correct, circuit execution continues through the "Cancel Temporary Programming" block, and out exit point 3 into the "Transmit Memory" block of FIG. 2C. The "Transmit Memory" signal is generated by program control logic 82 through signal path 87 to cause transmitter 91 to transmit back to the remote programming unit, the content of the memory or temporary data. After this transmission, circuit execution continues through the "Reset Programming Circuits and Timers 1 and 2" block and back to the start point.

In the case where parity is correct, program control logic 82 will cause the data in value storage reister 66 and parameter/value routing register 68 to be transferred in a parallel fashion to the corresponding value buffer 93 and parameter/value routing buffer 95. Buffers 93 an 95 are selectively connectable to the main memory 92 as provided for by program control logic 82 and signal path 83. Program control logic 82 responds to programming bits resident in the last two stages of register 68, via signal paths 84 and 86, to provide either a permanent write to the main memory, or to cause a temporary channeling of programing data through the main memory to the stimulation output circuit 94. Control over a permanent write or a temporary program write is provided for by signal path 85 which is connected between program control logic 82 and memory 92. The two possible modes of operation are reflected in the flow chart by the blocks entitled "Enable Temp Inputs" and "Write to Permanent Memory". After either operation, program execution continues to entry point 2 of FIG. 2C to the decision block entitled "Last Program Sequence?".

A decision to execute a memory transmit back to the remote programming unit is made by program control logic 82 in response to the signals present on signal paths 84 and 86, which as previously noted are connected to the last two stages of the parameter/value routing register 68. It will be seen then that a series of program sequences, or directions to write permanently or temporarily, are indicated to the program control logic 82 via the program data embedded in the third and fourth bits of each program sequence. In the case where a transmission back to the remote unit is desired, control logic/transmitter 91 is activated through signal path 87 from program control logic 82. In the preferred embodiment, a delay of 30 ms is employed between programming sequences to allow sufficient time for initialization of the decoding circuits.

When a programming operation is complete, the receiver is returned to its "watch" mode by timer 2, i.e. refresh timer 40, at the end of its time out interval. Conversly, if temporary programming is sought to be maintained while the stimulation output is monitored, or further programming is contemplated, the receiver may be maintained in an on-condition and the linkage of any temporary programming to the control circuits of the output stimulation circuits may be maintained by providing consecutive refresh code sequences at intervals sufficient to prevent sequence timer 69 from timing out.

FIGS. 5-9 comprise the detailed schematic diagram of the electronic circuitry of the present invention. Each of the FIGS. 5-8 include two sheets, A and B. For the convenience of the reader, the A and B sheets of these Figures may be lined up so as to facilitate locating of interconnecting lines when reading the specification. As a further aide, interconnections between different numbered figures are alphabetically labeled so as to be readily distinguishable from those interconnections between the A and B sheets of each Figure. While each line or conductor which interconnects the various drawings is labeled, it will be understood that some of the labels are solely for the purpose of showing the proper interconnection of the circuits, and that any particular line or conductor may not be specifically identified or recited in the specification. Also, although power supply and ground connections for the various components have been omitted from the schematic diagram for the sake of clarity, it will be understood that such connections may be of any conventional design known in the art.

The following explanation of FIGS. 5-9 will be made with reference to FIGS. 3A and 3B which are the corresponding detailed block diagram. Referring to FIG. 5, there is shown circuit 100 having an input a from a receiver circuit. The receiver circuit may be of any design providing for selective actuation thereof and capable of receiving and amplifying remotely generated RF signals so that they may be interfaced with the digital circuits of the present invention. Cricuit 100 corresponds to pulse shaping circuit 32 of the detailed block diagram. The output of circuit 100 is applied to NOR-gate 104, and the compliment thereof to the input of flip-flop 102. The SLCK (Conductor b) and XOSC signals are applied to gates 106 and 134 respectively. In the detailed block diagram, the SLCK signal generator is incorporated in receiver and decode control 34. The SLCK signal periodically clocks or strobes the receiver via NOR-gate 106 and conductor c, providing that flip-flop 102 is in a reset condition. Conductor c is analogous to signal path 36 of the detailed block diagram.

As explained earlier with reference to the detailed block diagram, the concurrence of a remotely generated program pulse at the receiver and a receiver activating strobe signal causes the receiver to be held in an active condition, as provided for by flip-flop 102 and NOR-gate 106. The reset input of flip-flop 102 is connected to conductor p, which is analogous to signal path 42 of the detailed block diagram.

When flip-flop 102 is set, pulses are fed through NOR-gate 104 and through conductors 114 and 112 into flip-flop 110 of data decode circuit 135. Data decode circuit 135 is represented in the detail block diagram by block 48; NOR-gate 104 is represented by data decode clock 44, which includes the XOSC signal generator. Circuit 135 includes flip-flop 130-132, flip-flops 110, 113, 115, 117 and 119 and the associated gates and inverters thereof. When the receiver is being held in an active mode, demodulator clock signal XOSC is fed through NAND gate 134, and inputted to flip-flop 130. XOSC is divided down to a signal having a 244 microsecond period, which is conveyed from the not-Q output of flip-flop 132 to the clocking inputs of flip-flops 113 and 115. In response thereto, flip-flop 113 produces a reset signal for input to flip-flops 115, 117 and 119. Using a timing scheme well known in the art, incoming program pulses are decoded according to the delays therebetween to produce "0" or "1" data at the not-Q output of flip-flop 119, which is connected through an inverter to conductor 133. The reset inputs of flip-flops 130-132 and 113 are connected to a conductor labeled POR for power-on-reset. The power-on-reset signal occurs once during the power up of the circuits of the implanted device, and functions to initialize the above-mentioned circuits and various others connected to the POR conductor, to a known condition necessary for the proper operation of the device's electronics.

Referring to FIG. 4 for a moment, it will be seen that in the preferred embodiment of the present invention a "1" data bit corresponds to a delay, between remotely generated programming pulses, of approximately 2.2 milliseconds, while a "0" data bit corresponds to a delay less than or equal to approximately 900 microseconds. Also, it will be seen that the data bits are clocked into the program registers upon the reception of a subsequent pulse. Referring back to FIG. 5, these clocking signals are conveyed on conductors 112 and 114 to the clocking inputs of the eight stage register comprised of flip-flops 120-128, which are functionally analogous to register 52 of the detailed block diagram; conductor 134 and conductors 112 and 114 are analogous to signal paths 50 and 54 respectively.

NAND gate 150 and its corresponding inputs and output is functionally represented by logic 51 of the detailed block diagram. NAND gate 150 has its output connected to conductor f, which corresponds to signal path 56 of the detailed block diagram, to provide a control input to NOR gate 202 of FIG. 6B.

Figure 6A:
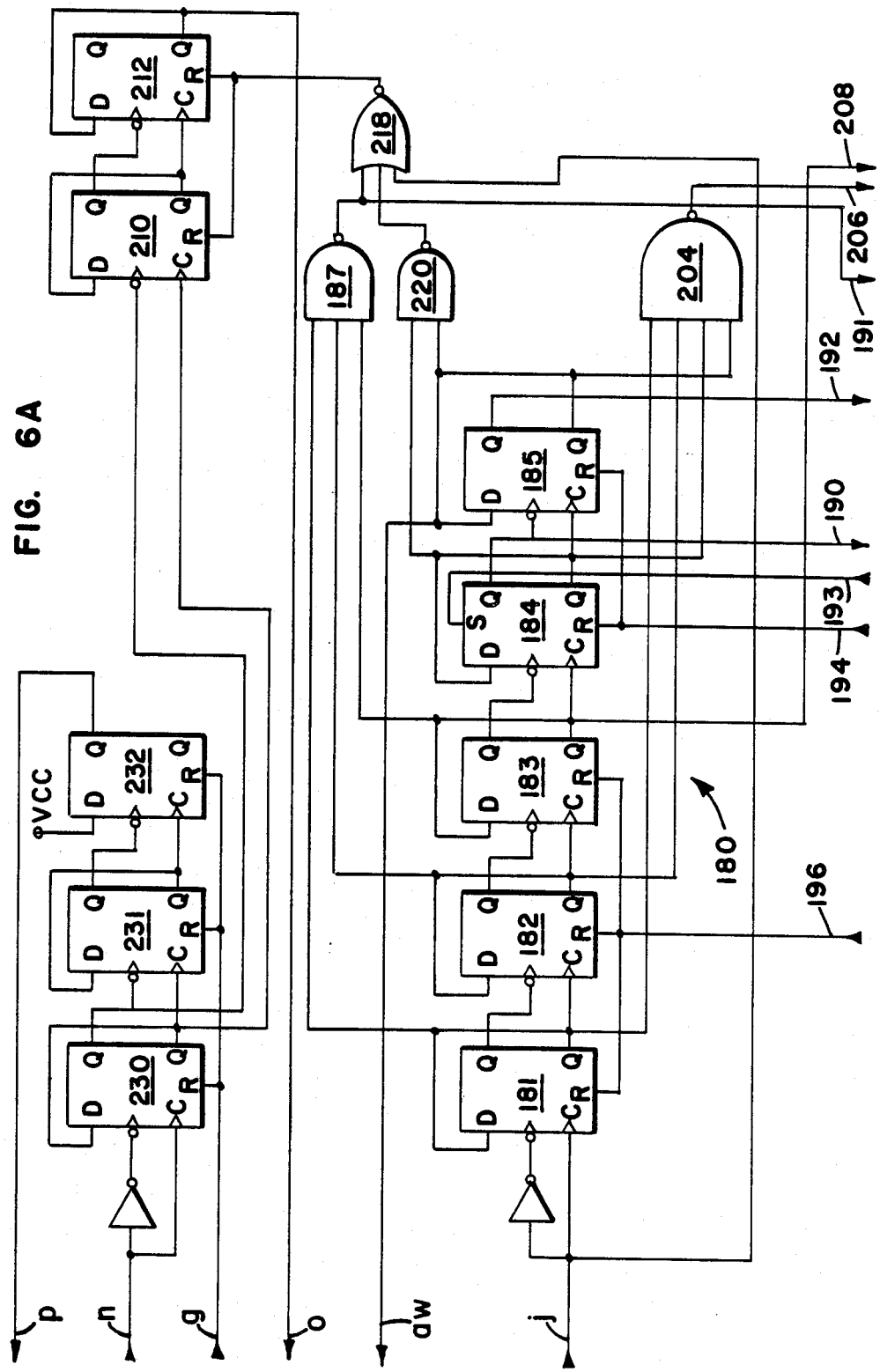
Figure 6B:
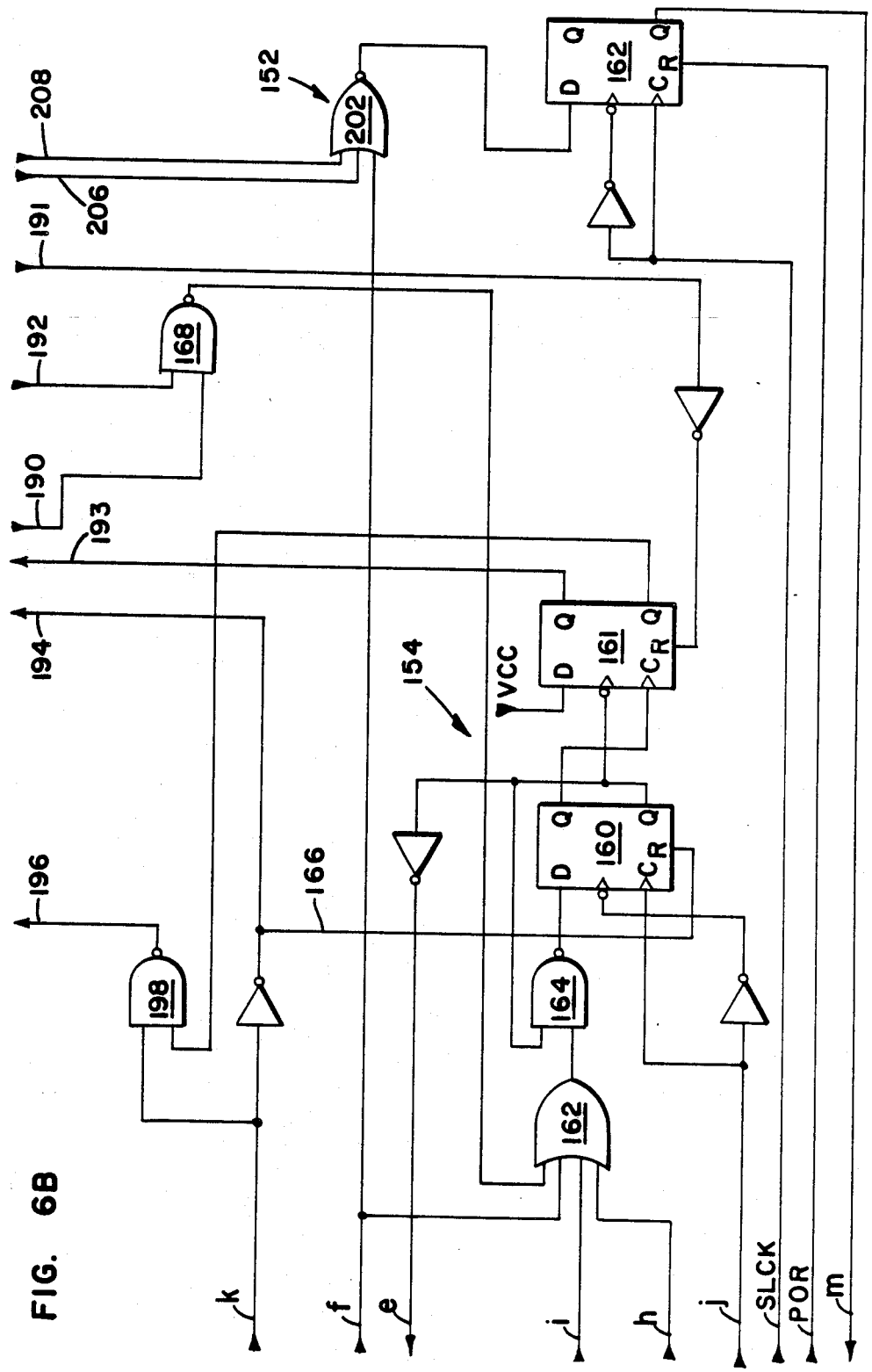
Figure 7A:
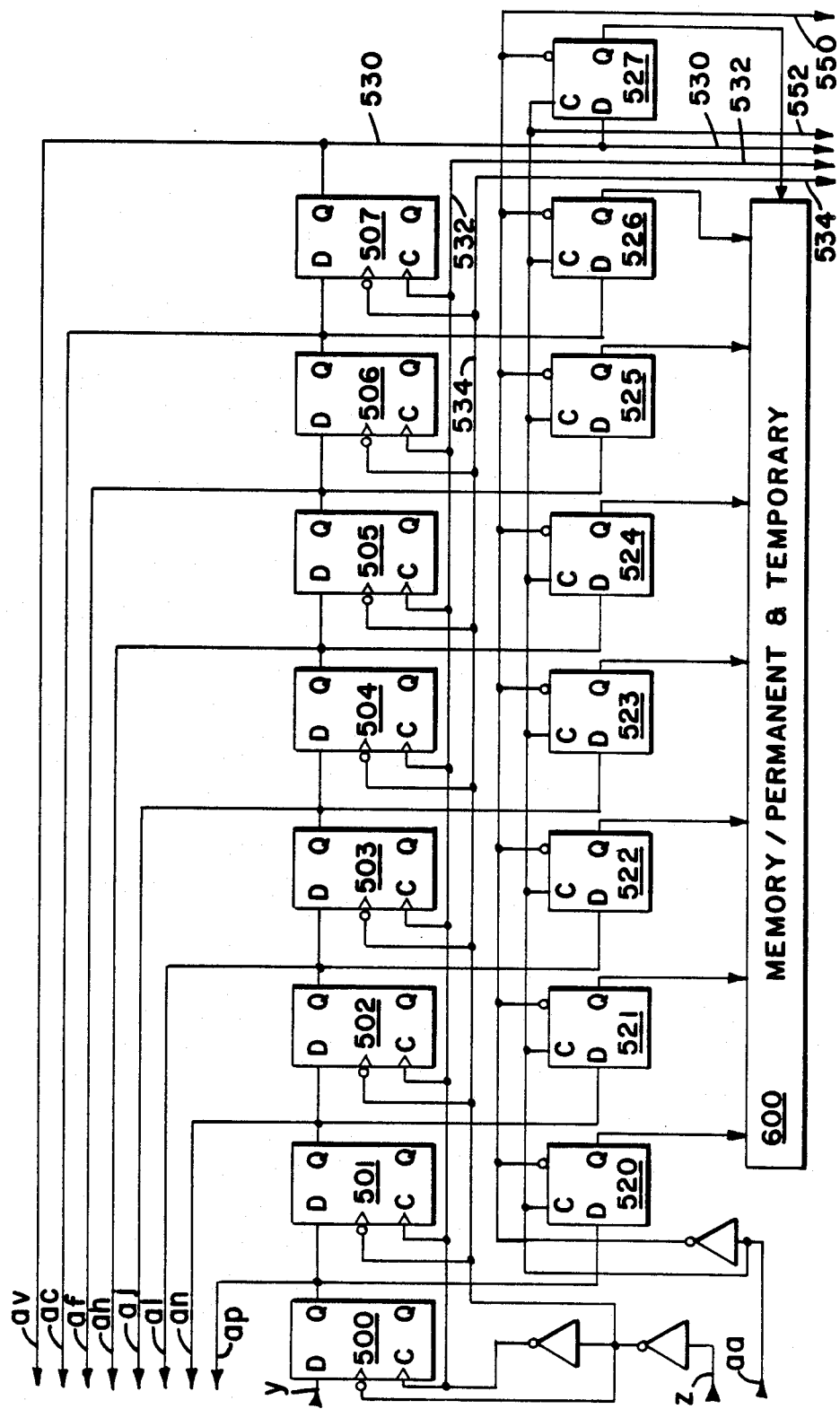
Figure 7B:
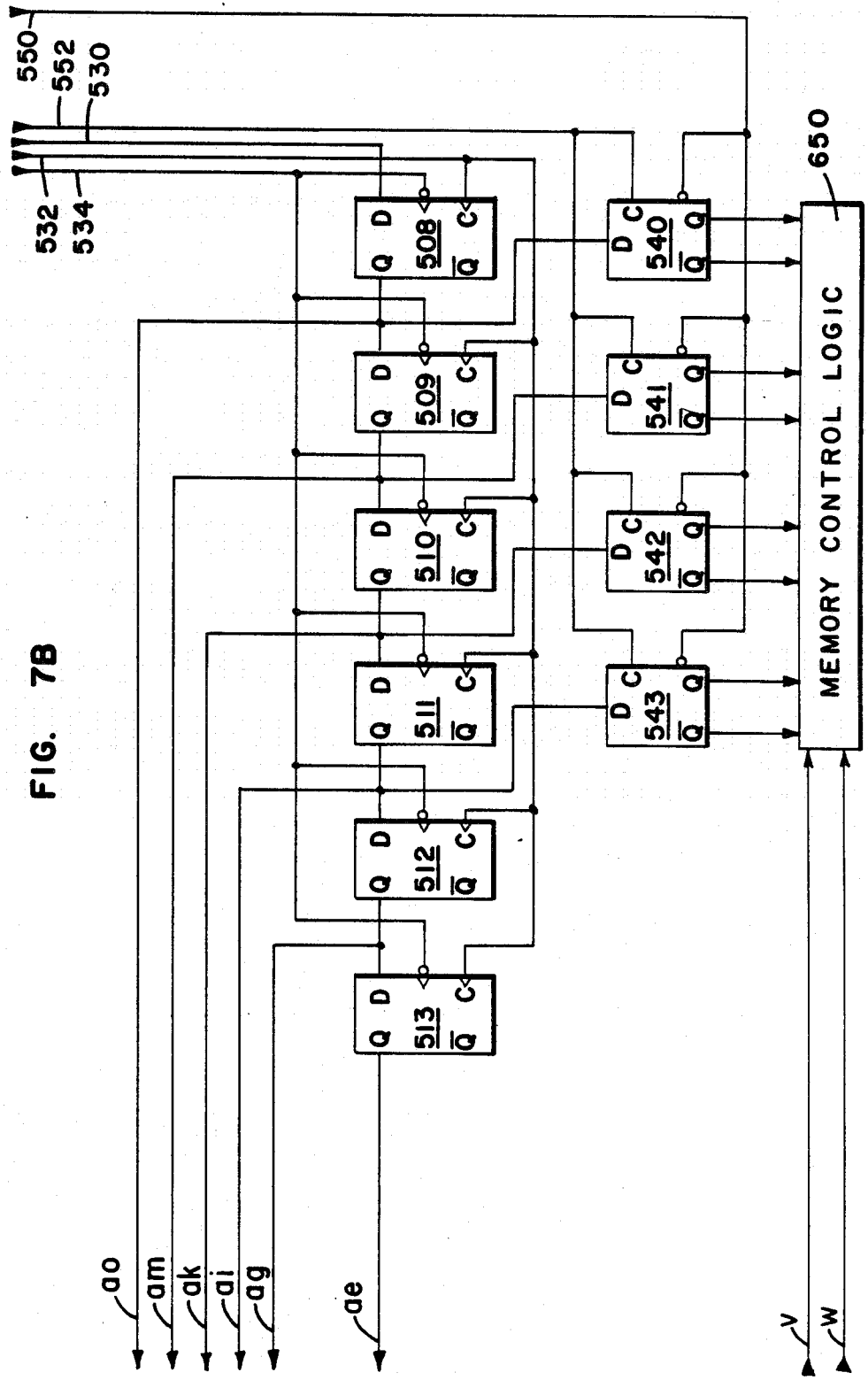

The detailed circuit schematic of refresh timer 40 of the detailed block diagram is found in FIG. 6A and comprises flip-flops 230-232. In the preferred embodiment the clocking signal for flip-flop 230 on conductor n is free running, and has a 62.5 millisecond period. For the sake of clarity the clock generator is not shown in the detailed schematic as it is a standard square wave generator well known in the art.

Figure 5A:
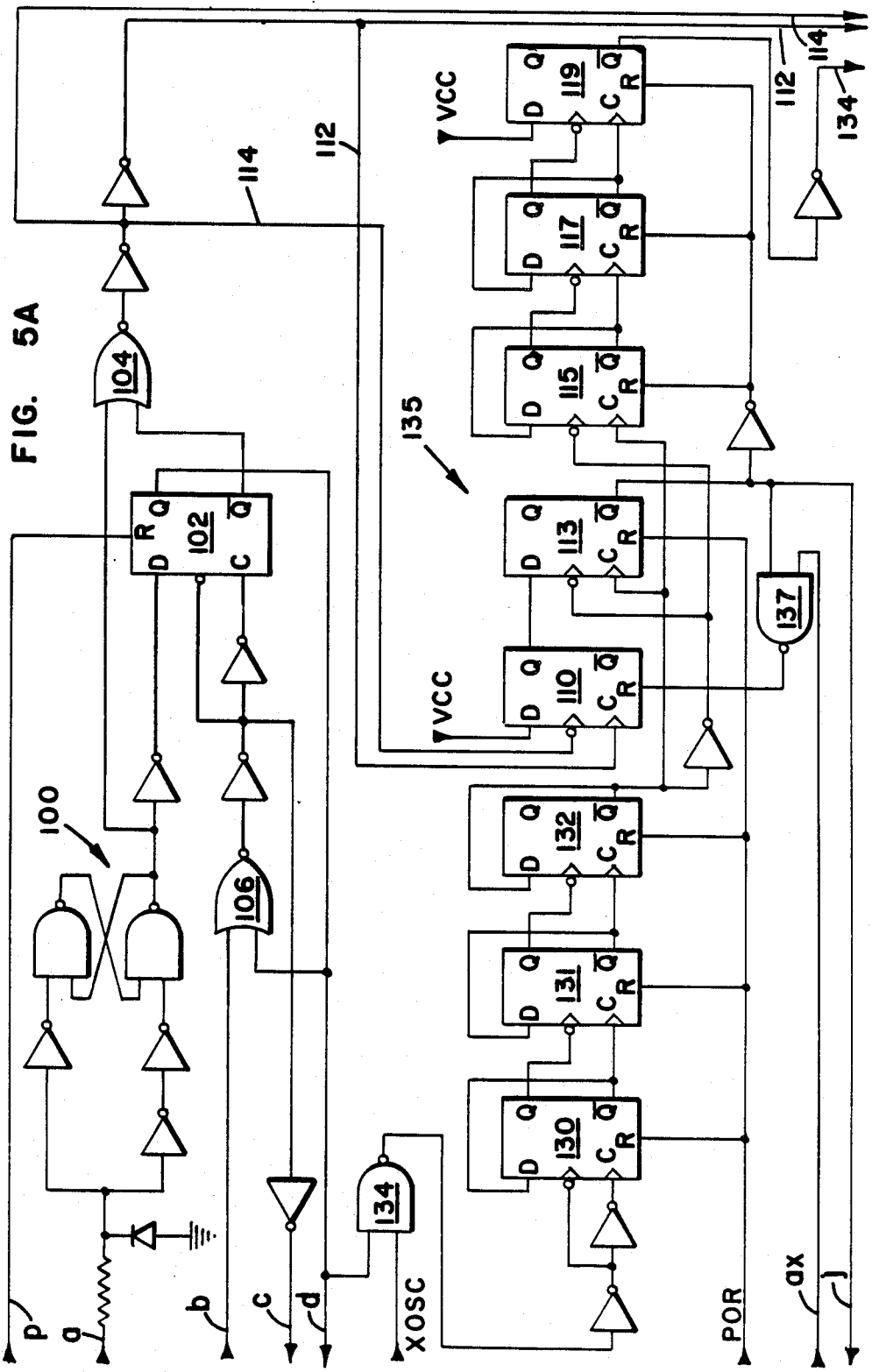
FIGS. 5A, 5B, 6A, 6B, 7A, 7B, 8A, 8B and 9 comprise a detailed schematic diagram of the electronic circuitry of the present invention.
Figure 5B:
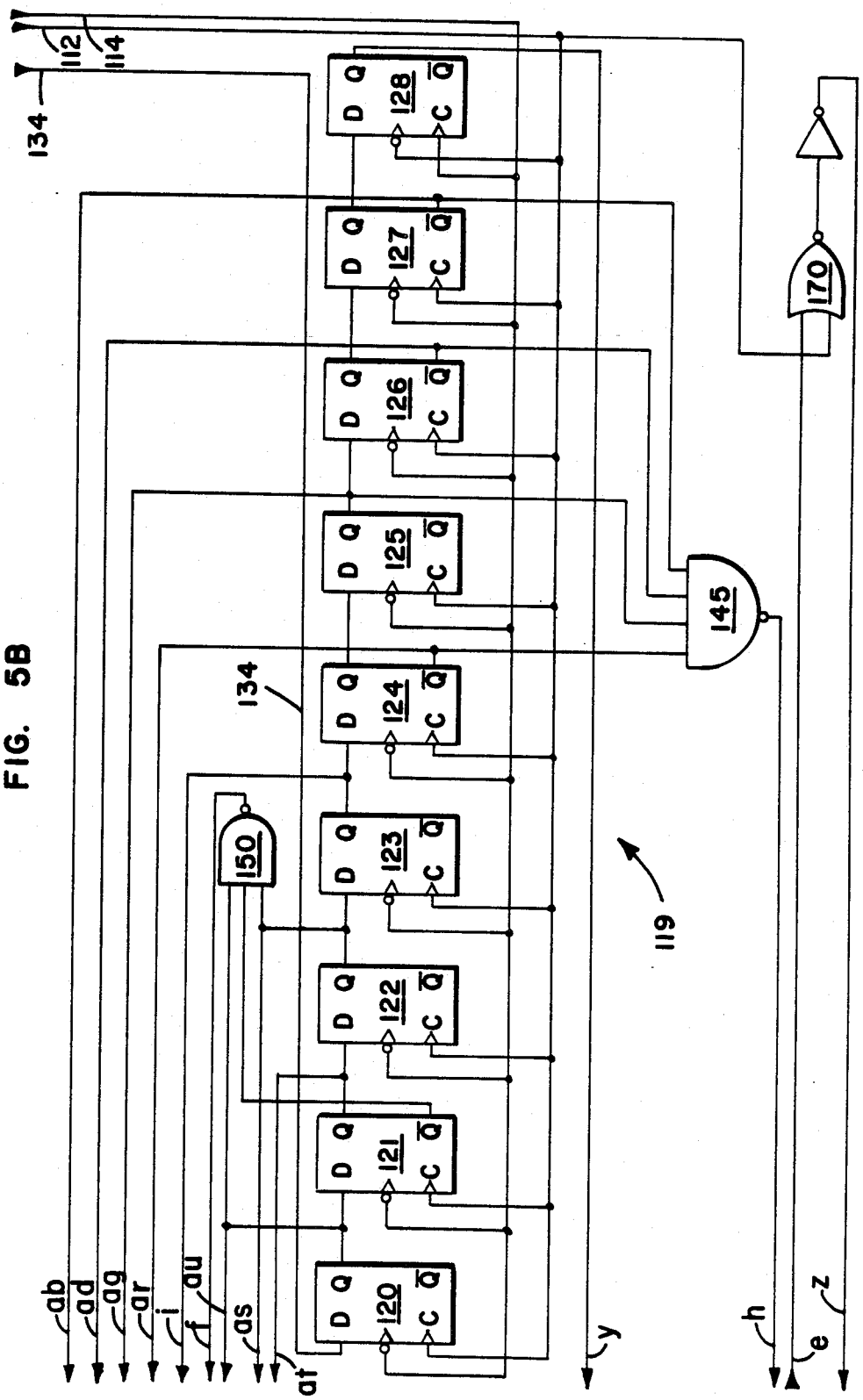

Output conductor p is connected to the Q output of flip-flop 232 and provides a reset signal to input latch flip-flop 102 of FIG. 5A. Flip-flops 210 and 212 are functionally analogous to sequence timer 69 of the detailed block diagram. They produce a time out signal on conductor o, which is connected to one input of NAND gate 345 of FIG. 8A after a time interval controlled by the 62.5 ms clock, providing that they are not reset before the end of the interval. NAND gates 187 and 220, which are connected to the not-Q outputs of flip-flops 181-185, cooperate with NOR gate 218 to control the reset input of flip-flops 210 and 212. Flip-flops 181-185 comprise the bit counter identified in the detailed block diagram with reference number 61. The not-Q outputs of flip-flops 181, 182, 184 and 185 are connected to the inputs of NAND gate 204. The output of NAND gate 204 is connected to conductor 206, which is connected to the input of NOR gate 202. The upper input of NAND gate 202 is connected to the not-Q output of flip-flop 183 via conductor 208, with the lower input connected to conductor g. Flip-flop 162, and gates 202 and 204 are functionally analogous to the refresh decode logic 58 of the detailed block diagram. When a pulse count equal to 4 is present in the bit counter flip-flops 181-185 and a binary 101 refresh code is detected by NAND gate 150, a refresh signal is generated by NOR gate 202 for input to flip-flop 162. Flip-flop 162 thereby generates a refresh reset signal on conductor m when clocked. Conductor m is analogous to signal path 57 of the detailed block diagram. Conductor m is connected to the input of NAND gate 310 of FIG. 8A.

Gate 162 and 164 and flip-flops 160 and 161 and the associated inverters thereof correspond in function to the access decode logic 75 of the detailed block diagram. The upper input of NOR gate 162 is connected to the output of NAND gate 168. The inputs of NAND gate 168 are connected to the last two stages of bit counter 180 via coductors 190 and 192, to produce a signal representative of a pulse count $\geq 24$. OR gate 162 has three other inputs. Input conductors g and h are connected from NAND gates 145 and 150 of FIG. 5B, which decode the eight bits or byte of information present in flip-flops 120–122 and 124–127. Input conductor i is connected to the output of flip-flop 123. When a proper access byte is present in flip-flops 120–127 and the pulse count is $\geq 24$ as is indicated by NAND gate 168, the output of OR gate 162 goes into a logic low condition. Assuming flip-flop 160 to be in a reset condition, NAND gate 164 responds to gate 162 by transitioning to a logic high, which clocks flip-flop 160 via conductor j. Flip-flop 161 responds to flip-flop 160 by setting flip-flop 184 via conductor 193 and causing the reset of flip-flops 181–183 via NAND gate 198 and conductor 196. The logic high signal generated on conductor e by flip-flop 160 is coneyed to NOR gate 170 of FIG. 5B and thereby disables further clocking signals from conductor 112 from propagating over conductor z to the clocking inputs of flip-flops 500–507 of FIG. 7A. Further control of the reset inputs to flip-flop 160 and flip-flops 181–185 is provided through conductor k, which is connected to the output of NOR gate 346 shown in FIG. 8A. One function of NOR gate 346 is to provide a reset signal to the access latch flip-flop 160 and bit counter flip-flops 181–185 when a time out of refresh timer flip-flops 230–232 occurs. In general, gates 310 and 344–346 are functionally represented in the detailed block diagram by refresh reset logic 60; NOR gate 170 is functionally represented by access gate 64; and conductor e functionally corresponds to signal path 76 of the same.

Figure 8A:
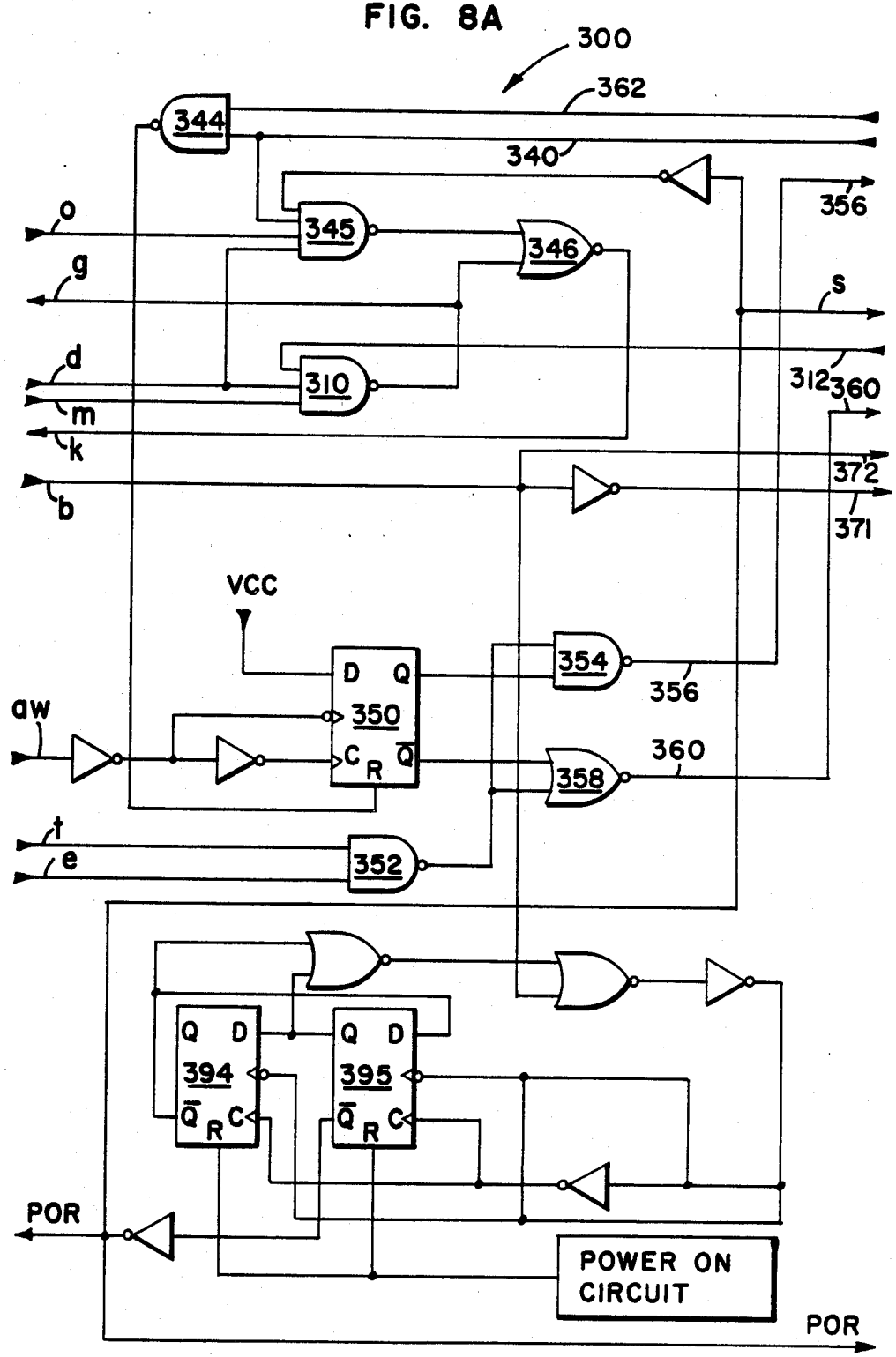
Figure 8B:
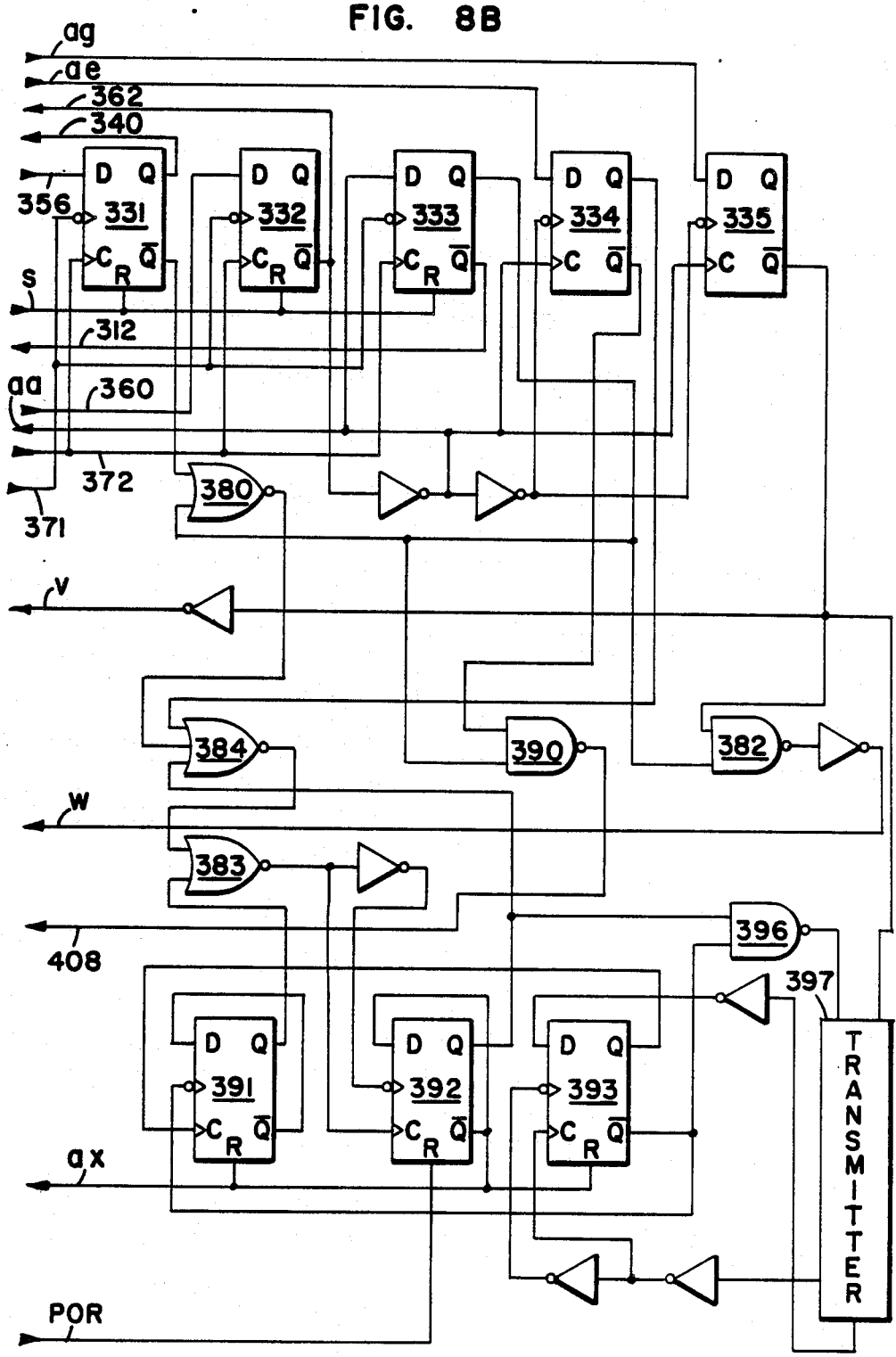
Figure 9:
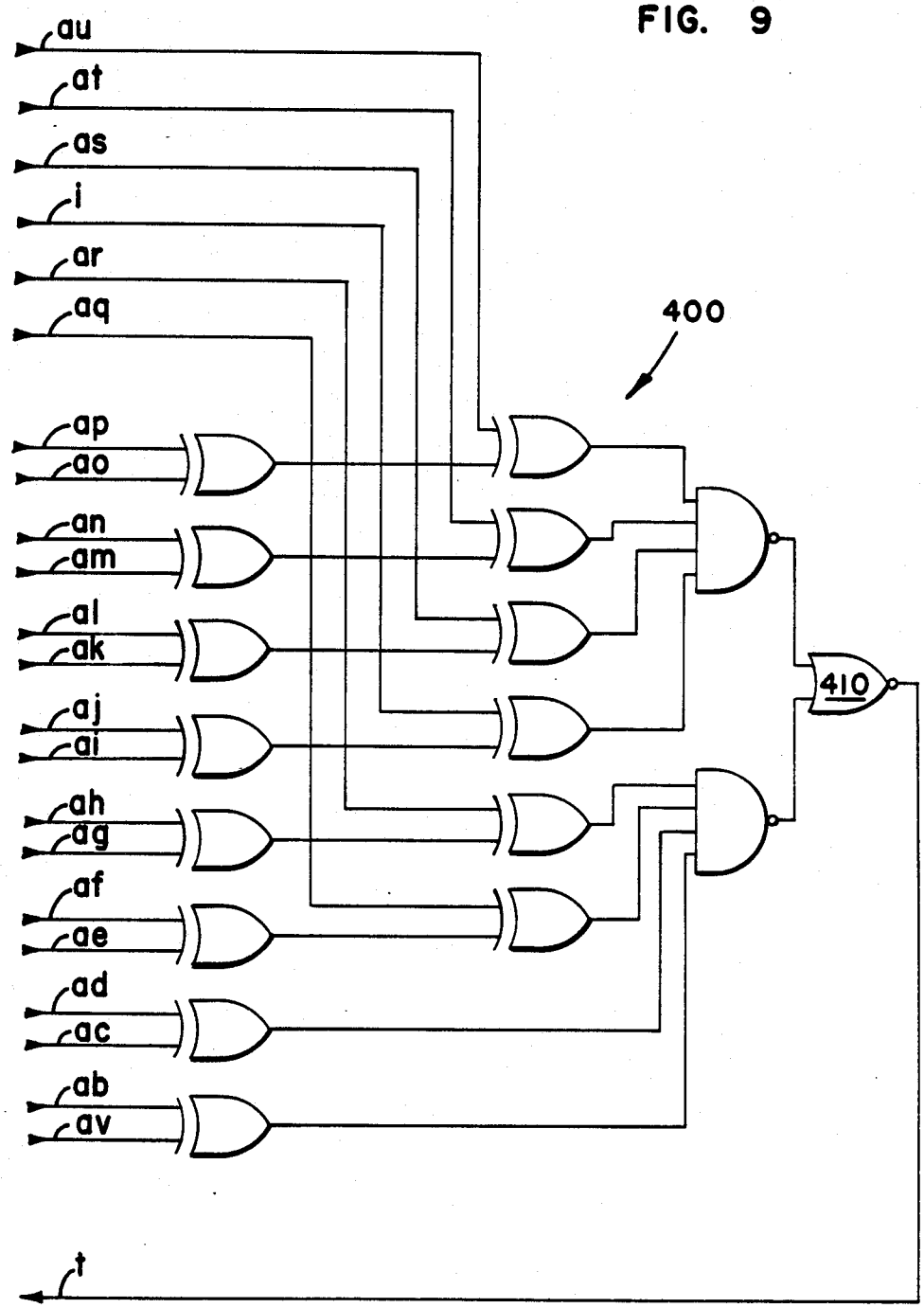

The parity logic and parity access logic identified by the respective reference numbers 53 and 81 in the detailed block diagram, may be found in FIGS. 8 and 9. In FIG. 8, flip-flop 350 and gates 352, 354 and 358 comprise the parity access logic. Flip-flop 350 is clocked by the last stage of the bit counter flip-flop 185 via conductor aw. This clocking occurs when the pulse count is equal to 32. The Q and not-Q outputs of flip-flop 350 are connected to the lower input of NAND gate 354 and the upper input of NOR gate 358 respectively. The other inputs of gates 354 and 358 are connected to the output of NAND gate 352. The upper input of NAND gate 352 is connected to conductor g, which is connected to the ouput of NOR gate 410 of parity logic 400 of FIG. 9. The inputs to parity logic 400 are derived from the outputs of flip-flops 500–513 of FIG. 7, and the outputs of flip-flops 120–127. This arrangement corresponds to that illustrated in the detailed block diagram. Conductor t corresponds to the output signal path 55 of parity logic 53 of the detailed block diagram.

The lower input of NAND gate 352 is connected to conductor e, which is connected to the flip-flop 160 output of access logic 154. Conductors 356 and 360, which are connected to the outputs of NAND gate 354 and NOR gate 358 respectively, are connected to the respective inputs of flip-flops 331 and 332. Depending on whether or not proper parity is present, flip-flops 331 and 332 produce and error reset signal or accept signal respectively. In either event flip-flop 350 is reset via NAND gate 344, which is connected to flip-flops 331 and 332 over conductors 340 and 362 respectively. In the case where access is correct, flip-flop 332 produces a logic 0 at its not-Q output which is in turn connected to conductor aa, which is connected to the D input of flip-flop 333, and the clocking inputs of flip-flops 334 and 335. A decision to temporarily link the program data into the output control circuits or to permanently write the data into the memory is accomplished by NAND gate 382. The upper input of NAND gate 382 is connected to the not-Q output of flip-flop 335, and the lower input connected to the Q output of flip-flop 333. Th D input of flip-flop 335 is connected to the output of flip-flop 512 through conductor ag. The logic state of flip-flop 512 thereby determines whether or not a temporary or permanent write will occur. The not - Q output of flip-flop 335 is connected to control circuits of the transmitter. The output of NAND gate 382 is inverted and connected to conductor w, which is connected to the memory control logic 650 of FIG. 7B. In FIG. 8A, flip-flops 394 and 395, and the associated gates and inverters thereof respond to a power-on signal from the power on circuit to produce the POR signal hereinbefore discussed. In general, the circuits of FIGS. 8A and 8B are functionally represented by program control logic 82 of the detailed block diagram.

Transmission by the implanted unit back to the remote programmer after a programming sequence is controlled by flip-flop 513, the logic state of which determines whether a further 32 bit programming sequence is forthcoming. Flip-flop 513 is connected to the D input of flip-flop 334 by conductor ae. The output of flip-flop 334 is connected to the upper input of NOR gate 384. The middle input of NOR gate 384 is connected to the output of NOR gate 380, which obtains inputs from the Q output of flip-flop 333 and the not-Q output of flip-flop 331. In the case where correct parity is present, NOR gate 380 presents a logic 0 to NOR gatee 384. the bottom input of NOR gate 384 is obtained from the Q output of flip-flop 392. The telemetry control circuits comprising flip-flops 391–393 and the associated gates thereof control the execution of teletransmissions via NAND gate 396. The connections of transmitter 397 to the memory circuits 600 are not shown, as the operation of those circuits are outside the scope of the present invention. The not-Q output of flip-flop 392 is connected to the reset inputs of flip-flops 391 and 393 into NAND gate 137 of FIG. 5A. During a telemetric transmission, NAND gate 137 holds flip-flop 110 in a reset condition and thereby disables the propagation of transmitted signals into the decode circuits 135.

In FIG. 7, flip-flops 500–507 and 508–513 correspond to the value storage register 66 and parameter/value routing register 68 respectively of the detailed block diagram. Flip-flops 520–527 and flip-flops 540–543 correspond to the value buffer 93 and parameter/value routing buffer 95 respectively, also of the detailed block diagram. During a programming sequence, data is clocked from the Q output of flip-flop 129 of FIG. 5B over conductor y and into the D input of flip-flop 500. Providing NOR gate 170 is enabled, i.e., the access is not latched, the data is serially propagated to flip-flop 507 and over conductor 530 into the D input of flip-flop 508. Flip-flops 508–513 are clocked with the same signal as flip-flops 500–507, with the clocking signals conveyed over conductors 532 and 534. After a programming sequence, and when proper parity has been achieved, buffer flip-flops 520–527 and 541–543 are clocked via conductor aa and its corresponding conductor 550. Conductor aa is derived from the not-Q output of flip-flop 332 of FIG. 8B. As discussed above, flip-flop 332 generates an accept data signal in response to the logic comprising gates 352, 354 and 358 and flip-flop 350. The outputs of buffer flip-flops 520–527 are connected to the memory/ permanent and temporary 600. It will be understood that memory 600 is controlled by memory control logic 650, even through the connections are not set out, for the purpose of clarity, in the drawing.

A general description of the layout and operation of the circuits of the detailed schematic diagram has been set forth in the above-text. Further details may be had with inspection of the detailed schematic diagram and reference to the other drawing and corresponding text.

It is contemplated that various other circuit designs may accomplish the operative scheme of the present invention. Therefore, it shall be understood that the invention is not limited to the particular embodiment set forth in the detailed schematic diagrams, but rather encompasses all equivalent designs within the spirit and scope set forth with respect to the more general block diagrams. Further, although the present invention is preferably embodied in an implanted device, it is contemplated that the invention may be utilized in other devices not of the implantable type to provide the same advantages set forth above.

What is claimed is:

1. Receiver apparatus for an implantable device of the remotely programmable type comprising:

an analog receiver operative when activated for receiving programming signals, including wakeup signals, from a remote programming unit;

digital circuit means for causing the receiver to be intermittently activated to watch for a remotely generated wake-up signal, said wake-up signal being of sufficient duration and period to coincide with an activated period of the receiver, the power consumption of said receiver being relatively higher when activated then when deactivated; and digital latching means for causing the receiver to be continuously activated for a predetermined time interval when a wake-up signal is detected by the receiver while intermittently activated so that a series of programming signals may be received.

2. A circuit according to claim 1 wherein said means for causing the receiver to be continuously activated further includes reset means responsive to more than one programming signal detected by the receiver while continuously activated for causing said receiver to be continuously activated for at least one more predetermined time interval.

3. A circuit according to claim 2 wherein said intermittent activation is periodic and wherein the periodic rate is greater than one millisecond and the duty cycle of intermittent activation is less than one-hundred microseconds.

4. Receiver apparatus for an implantable device of the remotely programmable type comprising:

an analog receiver operative when activated for receiving programming signals from a remote programming unit;

digital circuit means for recurringly activating the receiver at a low duty cycle so that the receiver intermittently surveys for remotely generated programming signals, the power consumption of said receiver being relatively higher when activated than when deactivated;

digital latching means connected to the receiver and responsive to the first programming signal detected by the receiver for holding the receiver in an activated condition for a predetermined time interval; and digital reset means responsive to more than one programming signal comprising a reset code detected by the receiver while held in said activated condition for causing said latching means to hold the receiver in an activated condition for another predetermined time interval.

5. A circuit according to claim 4 wherein said reset means includes a shift register for holding said more than one programming signal which comprises said reset code and selectively activated decode logic connected thereto for determining the presence of said reset code in the shift register.

6. A circuit according to claim 5 wherein said reset means includes a bit counter for activating said decode logic when a predetermined program signal count is reached.

7. A circuit according to claim 4 wherein said latching means includes a timer started by said first signal for timing said predetermined time interval.

8. A circuit for controlling the reception and decoding of remotely generated signals in an implantable device of the programmable type, comprising:

an analog receiver operative when activated for receiving programming signals from a remote programming unit;

digital circuit means for recurringly activating the receiver at a low duty cycle so that the receiver intermittently surveys for remotely generated programming signals, the power consumption of said receiver being relatively higher when activated than when deactivated;

digital latching means connected to the receiver and responsive to the first programming signal detected by the receiver for holding the receiver in an activated condition for a first predetermined time interval;

digital counting means for counting programming signals detected by the receiver;

digital reset means connected to said counting means and responsive to more than one programming signal comprising a reset code detected by the receiver while held in said activated condition for causing said latching means to hold the receiver in an activated condition for another first predetermined time interval and for resetting said counting means;

a programmable output circuit;

digital circuit means for linking a sequence of programming signals to the output circuit when a predetermined signal count is accumulated by said counting means; and digital sequence timing means for causing said counting means to reset at the end of a second predetermined time interval beginning when said counting means is reset, said second time interval having a duration relative to the duration of a valid programming sequence so that programming sequences not completed within said second predetermined time interval are prevented from linking to the output circuit.

9. A circuit according to claim 8 wherein said latching means includes a timer started by said first signal for timing said first predetermined time interval.

10. A circuit according to claim 9 wherein said latching means includes a flip-flop set by said first signal and reset by said timer at the end of said first predetermined time interval.

11. A circuit according to claim 8 wherein said reset means includes a shift register for holding said more than one programming signal which comprises said reset code and decode logic connected thereto for determining the presence of said reset code in the shift register.

12. A circuit according to claim 11 wherein said decode logic is activated by said counting means when a predetermined program signal count is reached.

* * * * *

UNITED STATES PATENT AND TRADEMARK OFFICE
CERTIFICATE OF CORRECTION

PATENT NO. : 4,676,248

DATED : June 30, 1987

INVENTOR(S) : Peter K. Berntson

It is certified that error appears in the above-identified patent and that said Letters Patent is hereby corrected as shown below:

Column 1, line 26, "accomodate" should be --accommodate--.

Column 4, line 21, "bits" should be --bits,--.

Column 4, line 35, "stimulationcontrol" should be --stimulation control--.

Column 5, line 3, after "correspond" insert --to--.

Column 5, line 22 "referesh" should be --refresh--.

Column 5, line 64 "routine" should be --Routine--.

Column 6, line 3 "circuit" should be --circuits--.

Column 7, line 28, "a" should be --an--.

Column 7, line 33, "futher" should be --further--.

Column 8, line 25, "reister" should be --register--.

UNITED STATES PATENT AND TRADEMARK OFFICE
CERTIFICATE OF CORRECTION

PATENT NO. : 4,676,248

DATED : June 30, 1987

INVENTOR(S) : Peter K. Berntson

It is certified that error appears in the above-identified patent and that said Letters Patent is hereby corrected as shown below:

Column 9, line 35, "Cricuit" should be --Circuit--.

Column 9, line 61 "flip-flop" should be --flip-flops--.

Column 11, line 31, "coneyed" should be --conveyed--.

Column 12, line 46, "gatee" should be --gate--.

Column 12, line 46 "the" should be --The--.

Signed and Sealed this

Twenty-fourth Day of November, 1987

Attest:

DONALD J. QUIGG

*Attesting Officer*  *Commissioner of Patents and Trademarks*